(12) United States Patent
Ross et al.

(10) Patent No.: US 8,676,256 B2
(45) Date of Patent: *Mar. 18, 2014

(54) SYSTEM AND METHOD FOR USER PROFILING FROM GATHERING USER DATA THROUGH INTERACTION WITH A WIRELESS COMMUNICATION DEVICE

(75) Inventors: David J. Ross, San Diego, CA (US); Eric C. Rosen, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/398,057

(22) Filed: Feb. 16, 2012

(65) Prior Publication Data

US 2012/0149993 A1      Jun. 14, 2012

Related U.S. Application Data

(63) Continuation of application No. 12/141,302, filed on Jun. 18, 2008.

(60) Provisional application No. 60/945,101, filed on Jun. 20, 2007.

(51) Int. Cl.
*H04M 1/00* (2006.01)

(52) U.S. Cl.
USPC ..... 455/556.1; 455/567; 455/419; 455/432.3; 600/300

(58) Field of Classification Search
USPC ........ 455/420, 418, 556.1, 412.2, 413, 414.1, 455/414.4, 419, 3, 567, 425, 432.2, 456.2, 455/552.1, 432.3; 705/1, 14.1, 14.25, 705/14.43, 14.49, 17, 21, 26, 64, 80, 14; 709/219, 204, 200, 203, 232, 234; 715/745; 725/14; 600/300

See application file for complete search history.

(56) References Cited

U.S. PATENT DOCUMENTS

| 5,490,275 A | 2/1996 | Sandvos et al. |
| 6,298,047 B1 | 10/2001 | Steffes et al. |

(Continued)

FOREIGN PATENT DOCUMENTS

| JP | 10136444 A | 5/1998 |
| JP | 2002142021 A | 5/2002 |

(Continued)

OTHER PUBLICATIONS

European Search Report—EP10155057—Search Authority—Munich—Apr. 12, 2010.

(Continued)

*Primary Examiner* — Tan Trinh
(74) *Attorney, Agent, or Firm* — Raphael Freiwirth

(57) ABSTRACT

A system, method, and wireless communication device that profiles a user thereof, or a user at a second wireless communication device in communication therewith. The wireless communication device gathers user data for a user thereof, or from a user at a second wireless communication device, and either directly generates, or has generated elsewhere, a user profile, such as a personality or psychological profile, or medical diagnosis of the user, and can display the user profile to the user and/or alter the wireless communication device functionality based upon the user profile. The gathered user data can be from physical user interaction with the wireless communication device, or from other equipment resident at the wireless communication device, such as a camera and medical diagnostic devices.

74 Claims, 6 Drawing Sheets

(56) References Cited

U.S. PATENT DOCUMENTS

| | | | |
|---|---|---|---|
| 6,754,470 B2* | 6/2004 | Hendrickson et al. | 455/67.11 |
| 7,212,990 B1 | 5/2007 | Greden et al. | |
| 2002/0049770 A1 | 4/2002 | Mayadas | |
| 2002/0055872 A1* | 5/2002 | LaBrie et al. | 705/14 |
| 2002/0069037 A1* | 6/2002 | Hendrickson et al. | 702/186 |
| 2003/0195934 A1 | 10/2003 | Peterson et al. | |
| 2004/0014423 A1 | 1/2004 | Croome et al. | |
| 2004/0168121 A1 | 8/2004 | Matz | |
| 2004/0177138 A1 | 9/2004 | Salle et al. | |
| 2005/0054381 A1 | 3/2005 | Lee et al. | |
| 2006/0183980 A1 | 8/2006 | Yang | |
| 2006/0217111 A1 | 9/2006 | Marolia et al. | |
| 2007/0073799 A1* | 3/2007 | Adjali et al. | 709/200 |
| 2007/0117557 A1 | 5/2007 | Adjali et al. | |
| 2007/0123222 A1 | 5/2007 | Cox et al. | |
| 2007/0155402 A1 | 7/2007 | Van | |
| 2008/0027992 A1 | 1/2008 | Vadavia et al. | |
| 2008/0086318 A1 | 4/2008 | Gilley et al. | |
| 2008/0255870 A1 | 10/2008 | Butler | |
| 2008/0318563 A1 | 12/2008 | Ross et al. | |
| 2009/0106664 A1* | 4/2009 | Corrao et al. | 715/745 |
| 2009/0113319 A1* | 4/2009 | Dawson et al. | 715/762 |
| 2009/0157714 A1 | 6/2009 | Stanton et al. | |
| 2010/0069040 A1 | 3/2010 | Nath et al. | |
| 2010/0144328 A1 | 6/2010 | Keating et al. | |
| 2012/0054680 A1 | 3/2012 | Moonka et al. | |
| 2012/0149360 A1 | 6/2012 | Ross et al. | |
| 2012/0157075 A1 | 6/2012 | Ross et al. | |
| 2013/0072169 A1 | 3/2013 | Ross et al. | |

FOREIGN PATENT DOCUMENTS

| | | |
|---|---|---|
| JP | 2002290508 A | 10/2002 |
| JP | 2006074477 A | 3/2006 |
| WO | WO2007044328 A2 | 4/2007 |

OTHER PUBLICATIONS

International Preliminary Report on Patentability, PCT/US2008/067773, International Preliminary Examining Authority, European Patent Office, Sep. 3, 2009.

International Search Report—PCT/US08/067773, International Search Authority—European Patent Office—Jan. 29, 2009.

Partial International Search Report—PCT/US08067773, International Search Authority—European Patent Office—Sep. 2, 2008.

Written Opinion—PCT/US08/067773, International Search Authority—European Patent Office—Jan. 29, 2009.

Partial European Search Report—EP10155057—Search Authority—The Munich—Apr. 12, 2012.

* cited by examiner

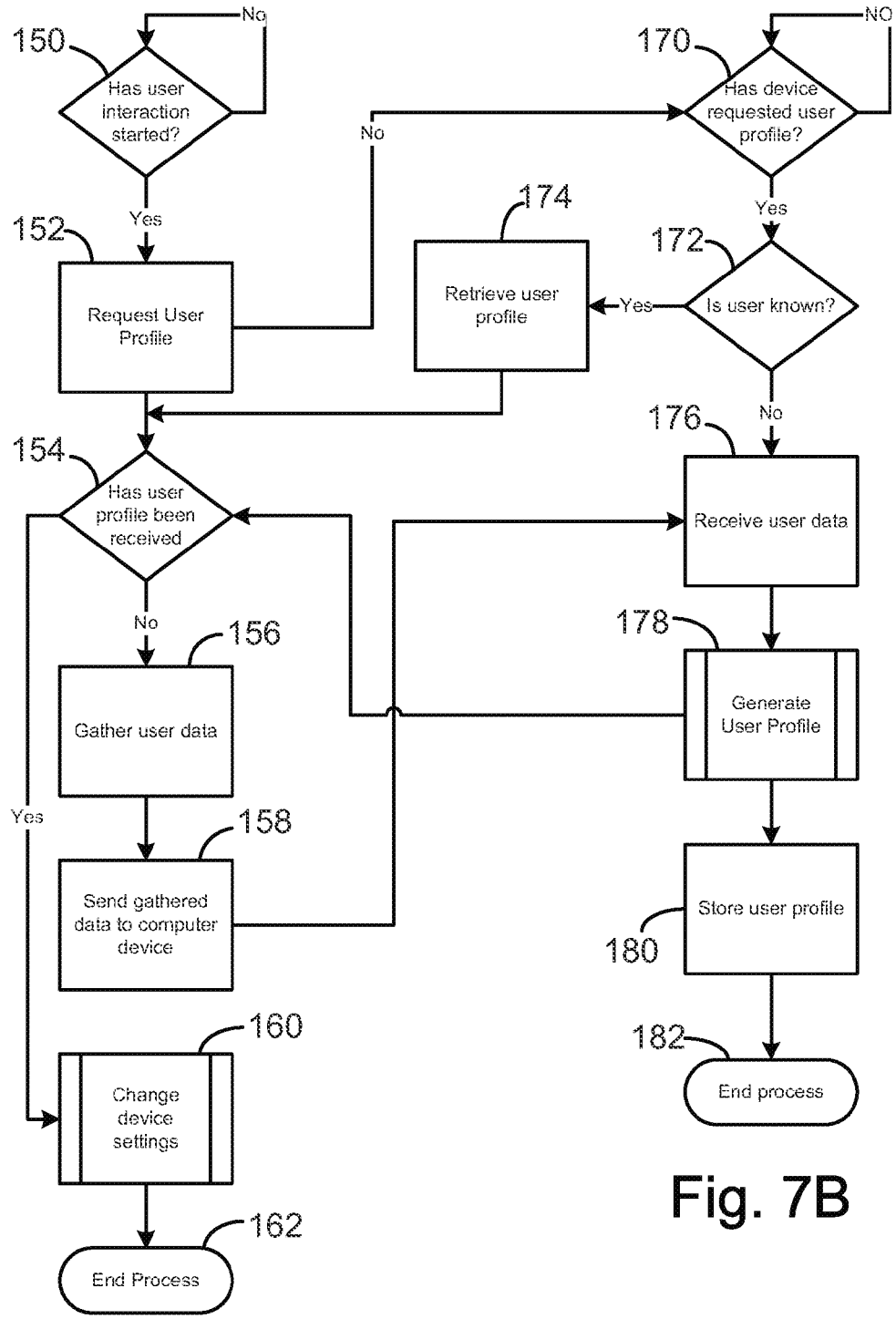

SYSTEM AND METHOD FOR USER PROFILING FROM GATHERING USER DATA THROUGH INTERACTION WITH A WIRELESS COMMUNICATION DEVICE

CROSS-REFERENCE TO RELATED APPLICATIONS

This application is a continuation of U.S. patent application Ser. No. 12/141,302 entitled "System And Method For User Profiling From Gathering User Data Through Interaction With A Wireless Communication Device" filed on Jun. 18, 2008 which claims the benefit of U.S. Provisional Patent Application Ser. No. 60/945,101, filed on Jun. 20$^{th}$, 2007. The contents of these documents are incorporated herein by reference. This application is also related to U.S. patent application Ser. No. 13/398,005 entitled "System And Method For User Profiling From Gathering User Data Through Interaction With A Wireless Communication Device," filed on Feb. 16, 2012 and U.S. patent application Ser. No. 13/398,179 entitled "System And Method For User Profiling From Gathering User Data Through Interaction With A Wireless Communication Device," filed on Feb. 16, 2012, and U.S. patent application Ser. No. 13/427,631 filed on Mar. 22, 2012, each of which claims the benefit of U.S. Provisional Patent Application Ser. No. 60/945,101, filed on Jun. 20, 2007.

BACKGROUND OF THE INVENTION

1. Field of the Invention

The invention relates to wireless communication devices that communicate across a wireless communication network. More particularly, the invention relates to a system and method for generating profiles for users of wireless communication devices based upon user interaction with the device.

2. Description of the Related Art

Existent computing devices, to include wireless communication devices such as mobile phones, personal digital assistants (PDAs), interactive pagers, and other wireless computer platforms can alter their interactive functionality with the user. Typically, the user configures the functional parameters of the device, such as the user interface (UI), navigation choices such as screen presentation, and other items such as ring tones and automatic turn-off. Most of these functions are not adjusted automatically by the device, but are set in default parameters by the vendor until specifically adjusted by the user. Mobile computing devices also typically have limited resources such as bandwidth, processing capability, and power such that it is always preferably to limit device activity to conserve the device resources.

There are some computer devices that attempt to learn the preferences of the user of the device based upon user interaction with the device. For example, a computer device will often implement a "most recently used" algorithm with device functionality, thereby assuming that the most recently used item or function of the user of the device is the one most likely to be next desired by the user. Computer devices typically use only rudimentary algorithms that try to predict user desire based upon simple patterns of usage of the device because a more complex algorithm will require too much of the mobile device resources to implement. Consequently, without user modification, the computer device will not automatically significantly alter the device functionality for the user.

It is therefore desirous to have an ability to adequately profile the user of a wireless communication device and selectively modify wireless communication device functionality, based upon the profile of the specific user, and it is to such a system and method to provide this ability that this invention is primarily directed.

SUMMARY OF THE INVENTION

Briefly described, the present invention includes a system, method, and wireless communication device that profiles a user thereof, or a user at a second wireless communication device in communication therewith. The wireless communication device gathers user data for a user thereof, or from a user at a second wireless communication device, and either directly generates, or has generated elsewhere, a user profile, such as a psychological profile or medical diagnosis of the user, and can display the user profile to the user and/or alter the wireless communication device functionality based upon the user profile. The gathered user data can be from physical user interaction with the wireless communication device, or from data other equipment resident at the wireless communication device, such as a camera and medical diagnostic devices.

In one embodiment, the wireless communication device collects data about the specific device user, and creates a particular psychological or personality profile for a user, and maps those scores either directly or indirectly into UI configuration, responses and behavior. The wireless device can also reconfigure itself for multiple users of the same device where those multiple users may have different personalities. When these wireless communication devices are then in communication with other user devices, the respective profile data can be used to aid the user communications with each other.

In one embodiment, the system for altering wireless communication device functionality for wireless communication devices on a wireless communication network, such alteration based upon the user profile of the user of the wireless communication device, includes at least one wireless communication device configured to gather user data from physical user interaction with the wireless communication device. The wireless communication device has a functionality for user interaction, and the device can selectively transmit the gathered user data across the wireless communication network. At least one computer device receives the transmitted gathered user data and creates user profile data based upon the received gathered user data, and then transmits the user profile data back to the at least one wireless communication device. The wireless communication device can alter the wireless communication device functionality based upon the received user profile data.

In one embodiment, the method of profiling a user of a wireless communication device and altering the wireless communication device functionality based upon the user profile includes gathering user data from physical user interaction with the wireless communication device, the wireless communication device having a functionality for user interaction, and creating a user profile based upon the gathered user data. Then the device can alter the wireless communication device functionality based upon the gathered user data.

In one embodiment, the wireless communication device has a wireless communication device functionality based upon a user profile and gathers user data from physical user interaction, then creates a user profile based upon the gathered user data. However, the wireless communication device can selectively alter functionality based upon the gathered user data, but does not have to do so. The wireless device can also be equipped to gather medical data of the user and make a medical diagnosis as a user profile.

Other advantages and features of the present invention will become apparent after review of the hereinafter set forth Brief Description of the Drawings, Detailed Description of the Invention, and the Claims.

BRIEF DESCRIPTION OF THE DRAWINGS

FIG. 7A is one embodiment of a method for sending gathered user data from a wireless communication device to another computer device executing a process shown in FIG. 7B, to receive a user profile back from the other computer device.

FIG. 7B is one embodiment of a method for creating and storing user profiles at a computer device based upon the gathered user data sent from the wireless communication device in FIG. 7A, and then sending user profiles back to the wireless communication device.

DETAIL DESCRIPTION OF THE INVENTION

In this description, the terms "communication device," "wireless device," "wireless communications device," "PTT communication device," "handheld device," "mobile device," and "handset" are used interchangeably. The terms "call" and "communication" are also used interchangeably. The term "application" as used herein is intended to encompass executable and non-executable software files, raw data, aggregated data, patches, and other code segments. The term "exemplary" means that the disclosed element or embodiment is only an example, and does not indicate any preference of user. Further, like numerals refer to like elements throughout the several views, and the articles "a" and "the" includes plural references, unless otherwise specified in the description.

Figure 1:
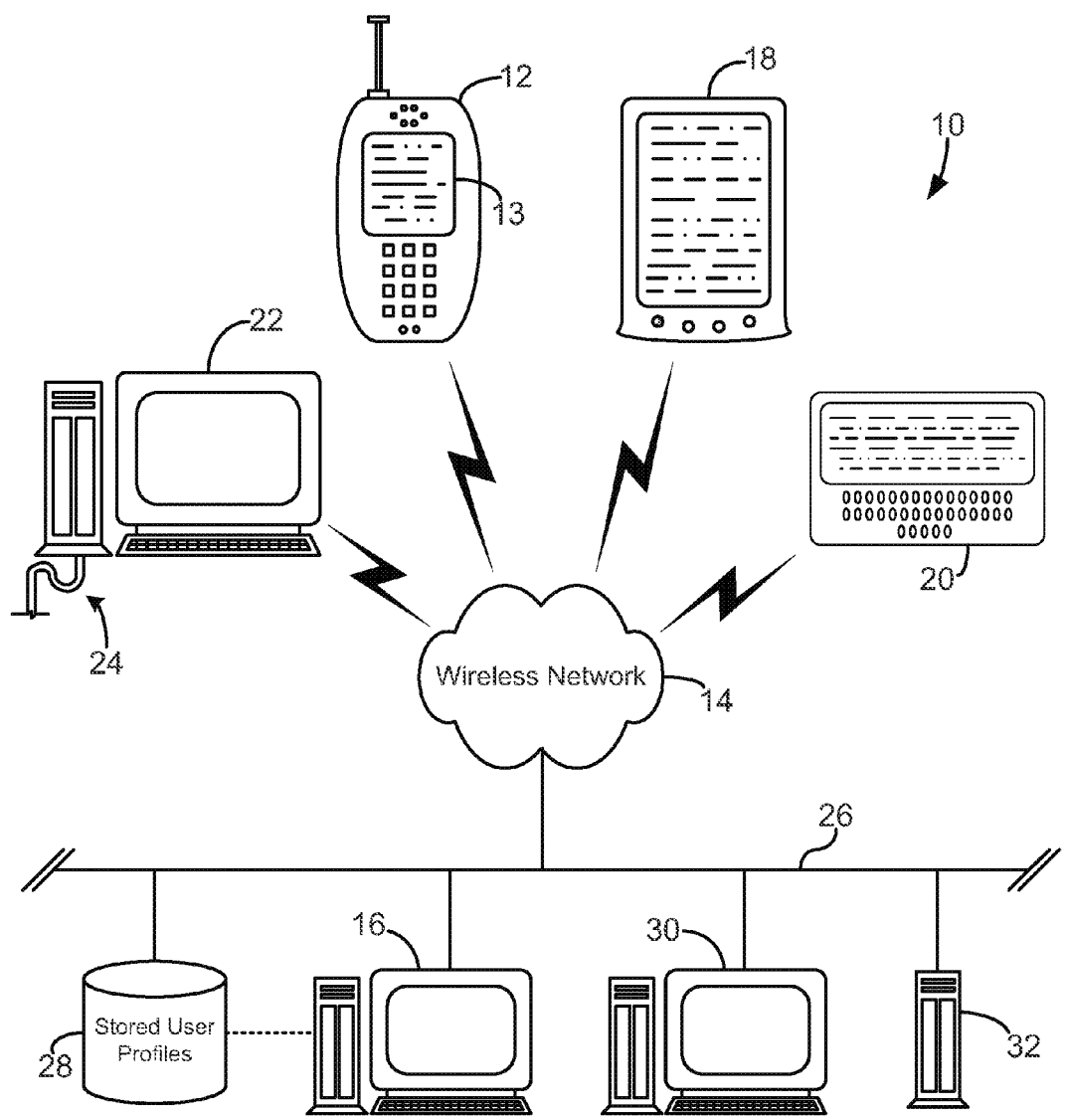
FIG. 1 is one embodiment of an architecture of a wireless communication network with a plurality of wireless communication devices communicating thereacross.

FIG. 1 illustrates one embodiment of the present inventive system 10 that allows wireless communication devices, such as mobile cellular telephone 12, in communication across a wireless network 14, with other computer devices, such as a user profile server 16, that selectively interacts with the wireless devices 12, 18, 20, 22 across a wireless communication portal or other data access to the wireless network 14 to gather user data from the devices 12, 18, 20, 22 and generate and return user profiles to the devices 12, 18, 20, 22 and can store user profiles in user profile database 28. Other computer devices, such as an application download server 30 and storage 32 can be available to the wireless communication devices 12, 18, 20, 22 either exclusively or in parallel to interaction with the user profile server 16 and resident on other networks, such as a local area network (LAN) 26.

As shown here, the wireless device can be a mobile cellular telephone 12, with a graphics display 13, a personal digital assistant 18, a mobile email device 20 with a graphics display, a which is shown here as a wireless device with qwerty capability such as a Blackberry® by RIM , or even a separate computer platform 22 that has a wireless communication portal, and may otherwise have a wired connection 24 to a network or the Internet. The system 10 can thus be performed on any form of remote computer module including a wireless communication portal, including without limitation, wireless modems, PCMCIA cards, access terminals, personal computers, access terminals, telephones without a display or keypad, or any combination or sub-combination thereof. Further, the term "application" as used herein is intended to encompass executable and nonexecutable software files, raw data, aggregated data, patches, and other code segments.

Figure 3:
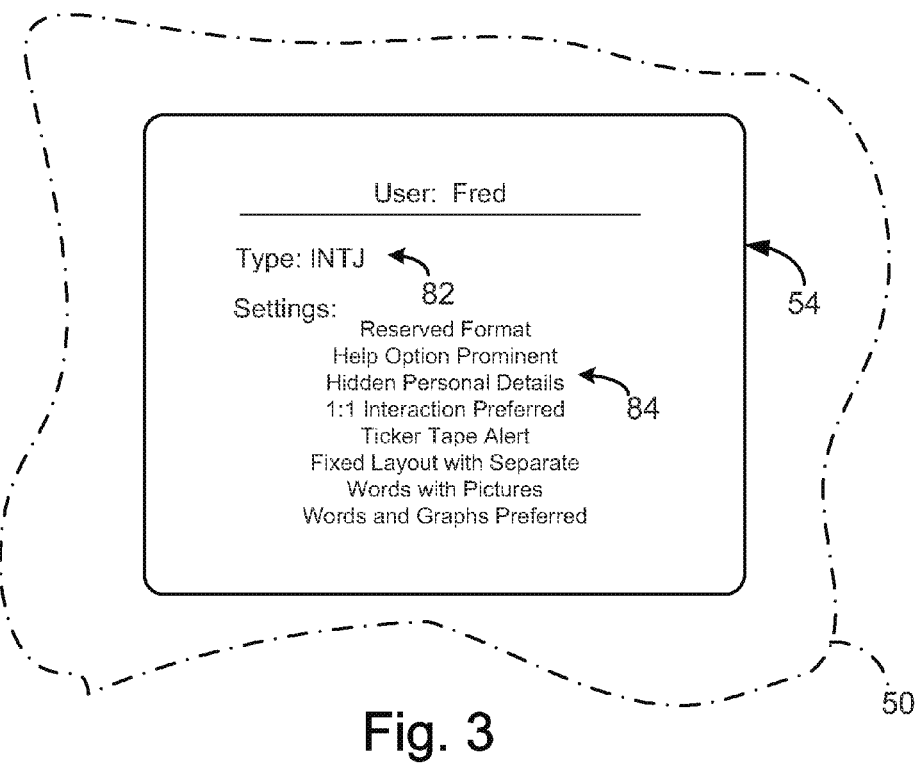
FIG. 3 is a screen shot for the display of the wireless communication device illustrating a personality profile for a user of the device.
Figure 4:
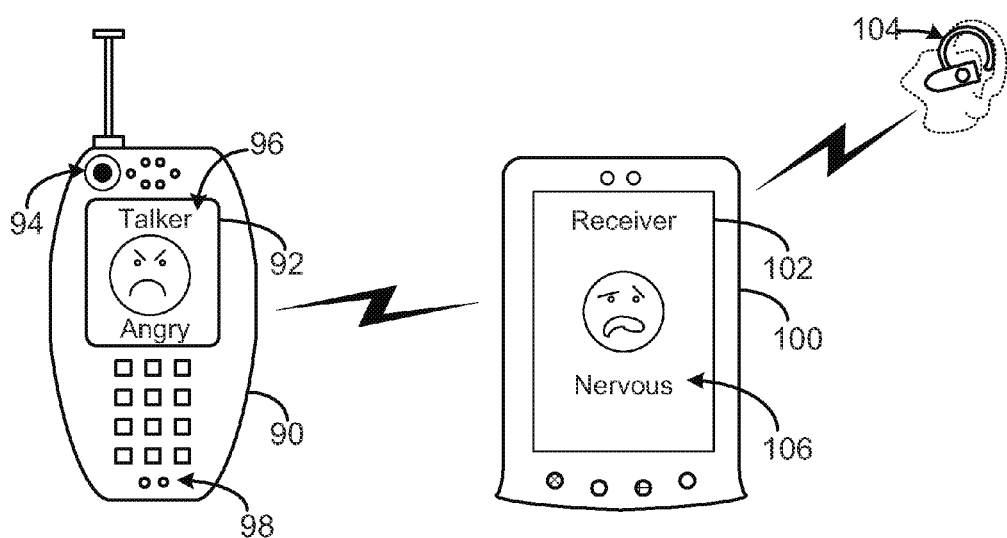
FIG. 4 is a representative diagram illustrating one embodiment of the invention wherein two communicating devices are showing the short-term emotional profile for the user of the other wireless communication device.

In overview, the system 10 allows the wireless communication devices 12, 18, 20, 22 to alter their functionality based upon a specific user profile generated from the user of the wireless communication device 12, 18, 20, 22. The system 10 also enables the wireless communication devices 12, 18, 20, 22 to create user profiles for other users during interaction with other wireless communication devices. As is more fully described below, at least one wireless communication device 12, 18, 20, 22 is configured to gather user data from physical user interaction with the wireless communication device 12, 18, 20, 22, wherein the wireless communication device has a functionality for user interaction, such as a specific UI as shown in FIGS. 3 and 4. In this embodiment of the system 10, the wireless communication device 12, 18, 20, 22 selectively transmits the gathered user data across the wireless communication network 14 to, at least, the user profile server 16, which is configured to receive the transmitted gathered user data, and which creates user profile data (such as a personality profile as described herein) based upon the received gathered user data. The user profile server 16 transmits the user profile data to the sending wireless communication device 12, 18, 20, 22, and the wireless communication device 12, 18, 20, 22 can alter wireless communication device functionality based upon the received user profile data. As shown further below, the user profiling can also occur completely at the wireless communication device 12, 18, 20, 22.

Figure 2:
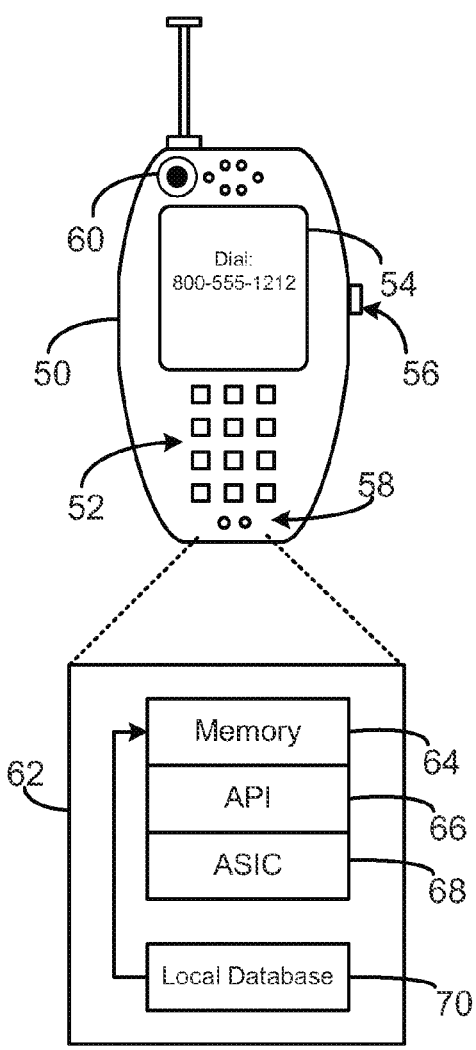
FIG. 2 is an representative diagram illustrating a mobile telephone as a wireless communication device, with a block diagram of the resident computer platform.

As particularly shown in FIG. 2, the wireless communication device, as embodied here is a mobile telephone 50 having a computer platform 62. The mobile telephone 50 has a numeric keypad 52, a graphic display 54 through which is implemented a user interface (UI), a microphone 58, and a group communication activator, or here, a push-to-talk button 56, and a camera 60. There are other devices and components known in the art that can be placed on the wireless communication computer platform 62 and utilized by the user and/or the computer platform 62 of mobile telephone 50.

The computer platform 62 can receive and execute software applications transmitted from the application download server 30. The computer platform 62 includes, among other components, an application-specific integrated circuit ("ASIC") 68, or other processor, microprocessor, logic circuit, programmable gate array, or other data processing device. The ASIC 68 is installed at the time of manufacture of the wireless device and is not normally upgradeable. The ASIC 68 or other processor executes an application programming interface ("API") layer 66 that interfaces with any resident programs in the memory 64 of the wireless device. The memory can be comprised of read-only or random-access memory (RAM and ROM), EPROM, EEPROM, flash cards, or any memory common to computer platforms. The computer platform 62 also includes a local database 70 that can hold the software applications not actively used in memory 64, such as the software applications downloaded from the application download server 30. The local database 70 is typically comprised of one or more flash memory cells, but can be any secondary or tertiary storage device as known in the art, such as magnetic media, EPROM, EEPROM, optical media, tape, or soft or hard disk. The user profiling can therefore be held in the local database 70 and implemented on the computer platform 62 when required.

In general, mobile telephones and telecommunication devices, such as cellular telephone 50, are being manufactured with increased computing capabilities and are becoming tantamount to personal computers and hand-held personal digital assistants ("PDAs"). These "smart" cellular telephones allow software developers to create software applications that are downloadable and executable on the processor, such as ASIC 68, of the cellular device. The downloaded data or executed applications can be immediately displayed on the display 54 or stored in the local database 70 when not in use. Likewise, the application can execute automatically or transparently to the user. The software applications can be treated as a regular software application resident on the wireless device 12,18,20,22, and the user can selectively upload stored resident applications from the local database 70 to memory 64 for execution on the API 66. The user of the wireless device 12,18,20,22 can also selectively delete a software application from the local database 70. As a result, end-users of the mobile telephones 50 can customize their telephones with programs, such as games, printed media, stock updates, news, or any other type of information or program available for download from application download servers through the wireless network 14.

In operation, the wireless communication devices 12, 18, 20, 22 gather user data either directly from the user from interaction, such as asking the user a series of questions and/or can make observations of the user and interpret the data, such as through sensing devices like the camera 60 and microphone 58. The wireless communication device 12, 18, 20, 22 can also collect data about the user from another device, such as user profile server 16, or wireless communication device 12, 18, 20, 22, via direct connection or through the Internet. The user data is preferably collected and updated periodically for the purpose of generating a user profile, such as a personality profile, a psychological type, a medical diagnosis, or an emotional state. The user profile can be for the "short-term," such as for user data gathered in a current communication or can be "long-term," or based upon a history of user interaction. The user profile can be used in supplement with other configuration data to deliver a user experience which would be most compatible, entertaining, and productive for the end user of the wireless communication device 12, 18, 20, 22. As used herein, the term "physical interaction" is meant to encompass the range of user interaction, such as physical contact with the device buttons, keypad 52, and other direct contact, and can also encompass data sensed from the user by the wireless device 12, 18, 20, 22, such as pictures taken from the camera 60, or medical information taken from a medical device, such as a remote earpiece, voice volume, speech patterns, and the like.

Figure 5:
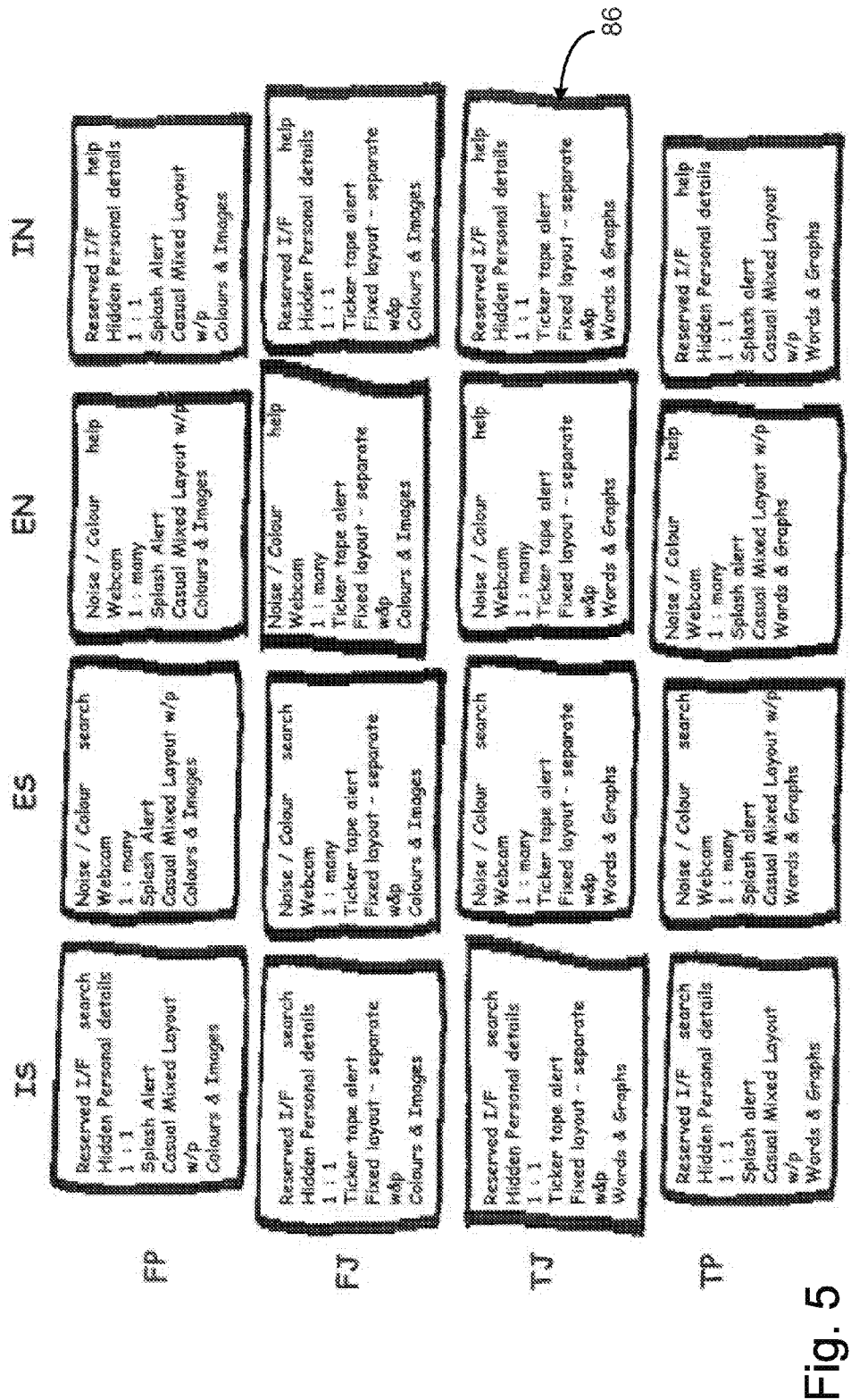
FIG. 5 is a chart illustrating one embodiment of user interface (UI) configurations for a wireless communication device based upon a generated user profile being a personality type.

As an example, a wireless communication device, such as mobile phone 50, has the ability to support multiple UI configurations and have multiple possible dialogs, functions, applications and contexts within those configurations. The mobile phone 50 could either recognize the user thereof via user input, such as a PIN number, use biometric data, such as a fingerprint reader, voice pattern recognition or face recognition (microphone 58, camera 60), or request identification of the user. The device would present the user with visual and verbal UI clues for its use that are compatible and harmonious with the user's personality (such as the UI configurations illustrated in FIG. 5). The wireless computer device 12, 18, 20, 22 will perform specific applications or behaviors based on the personality of the user in addition to more common UI behaviors. The mobile phone 50 can therefore leverage applications for the user that are compatible and harmonious with the user's personality and any situational data (inputs from the camera 60, microphone 58, or any other sensors). The wireless communication device 12, 18, 20, 22, can also be directly in communication with the user profile server 16, thus having significant resources available to generate many types of profiles or scores to be leveraged by the user interface or other device functionality, such as a personality score, an Intelligence Quota (IQ) score, cultural score, and religion score.

Other computer devices, such as wireless communication devices 12, 18, 20, 22, user profile server 16 or other devices on the wireless network 14, and applications on those devices that are connecting to the wireless communication device 12, 18, 20, 22 that stores a user profile, can selectively have access to the user profile in order to aid the calling party or application to communicate better with the user. The permission to access the data can be limited by the system 10, or only permissible through user allowance.

There are several personality tests known that give one insight into the behavior of a person, and the system 10 and wireless devices 12, 18, 20, 22 can individually or in tandem take gathered user data and execute a personality test on the user to try to determine user preferences and behavior. For example, one well known personality test is the "Myers Briggs" personality test. In simple overview, there are four categories of personality that are tested and evaluated. The first is "introversion" and "extroversion". These attitudes show how a person orients and receives their energy. In the extroverted attitude the energy flow is outward, and the preferred focus is on other people and things, whereas in the introverted attitude the energy flow is inward, and the preferred focus is on one's own thoughts and ideas.

Another attitude is "sensing" and "intuition," which are the perceiving functions. They indicate how a person prefers to receive data. Sensing prefers to receive data primarily from the five senses, and intuition prefers to receive data from the unconscious, or seeing relationships via insights. A third attitude is "thinking" and "feeling," which are the judging functions. Thinking uses logical "true or false," if-then logical connections. Feeling uses "more or less, better-worse" evaluations. When Thinking or Feeling is extroverted, judgments tend to rely on external sources and the generally accepted rules and procedures. When introverted, Thinking and Feeling judgments tend to be subjective, relying on internally generated ideas for logical organization and evaluation. The fourth attitude is "judging" and "perceiving," which reveal the specific attitudes of the functions. Judging types tend to prefer a step-by-step approach to life, relying on external rules and procedures, and preferring quick closure. The perceiving function is the direct opposite to the judging function. This can result in a "bouncing around" approach to life, relying on subjective judgments, and a desire to leave all options open. The four attitudes can be placed into a chart, like that shown in FIG. 5, and the wireless communication device 12, 18, 20, 22 can accordingly set the device functionality based upon what personality the user is believed to be. The chart in FIG. 5 thus contains device UI predetermined settings for all potential Myers Briggs personality types.

As shown in the example of FIG. 3, the display 54 of the mobile phone 50 can show the determined user profile for the user of the mobile phone 50, which here is the Briggs Myers personality evaluation, to the user. The user has been determined to be an INTJ, shown at arrow 82, with the device functionality set accordingly, as shown at arrow 84 (Box 86 in FIG. 5). This user profile can be based upon long-term user interaction with the wireless communication device 12,18, 20,22, or can be updated in the short-term, such as in the conversation shown in FIG. 4. Likewise, the same user profile can be generated for another user of a communication device, such as shown and described below relative to FIG. 8.

In FIG. 4, an active communication is occurring between mobile phone 90 and mobile wireless platform 100 where the emotion of the speakers engaged in a conversation is profiled and the profile is communicated to the other device such that the users of the devices know what the emotional state of the other user is. The mobile phone 90 includes a display 92, and a camera 94. The mobile wireless platform 100 includes a display 102 and also a remote earpiece 104. In this embodiment, the remote earpiece 104 also includes a medical diagnostic device that senses the blood pressure of the wearer (user). The user profiling in this communication typically occurs in the short-term in this embodiment, virtually in real time because emotions are being profiled. Here the receiving device is the mobile phone 90, and the talker, mobile wireless platform 100, is indicated as being angry which is shown on the mobile phone 90 in graphic 96. Here, the indication of anger comes from the blood pressure data taken from the user at remote earpiece 104, and the mobile wireless platform 100 sends the angry profile to the mobile phone 90.

In parallel, the mobile phone 90 gathers user data from the microphone 98 from the user who is speaking and the voice can be analyzed to indicate stress, which implies nervousness. The nervousness profile is then sent from the mobile device 90 to the mobile wireless platform 100. The receiver is then indicated as nervous on the display 102 of the mobile wireless platform 100, as shown at graphic 106. Such a presentation can be done in split-screen such that the user of the device sees both the profile being sent to the other device and the profile from the other device.

The gathering of user data can therefore be based upon interpretation of short-term data input by the user into the wireless communication device, such as the volume of the voice of the speaker, the pressure the user uses to press the keys (such as at keypad input 52 in FIG. 2), and a picture of the user (such as at camera 60). If the wireless communication device 12, 18, 20, 22 includes a medical diagnostic device, such as the remote earpiece 104 in FIG. 4, the short-term profile can be a medical diagnosis or other emotion or personality profile based upon gathered medical data. The gathering of short-term user data can also be based upon interpretation of data input by the user into the wireless communication device 12, 18, 20, 22, such as a direct questionnaire of the user.

The gathering of user data can also be based upon long-term user interaction with the wireless communication device 12,18,20,22. For example, the gathering of user data can be based upon interpretation of a contact list resident in the wireless communication device 12,18,20,22, or the interpretation of the number of members of one or more communication groups for the wireless communication device. Accordingly, a large number of contacts or group communication members would indicate extroversion in terms of the Myers Briggs personality test. The long-term interaction of the user with the wireless communication device 12,18,20,22 can be based upon any gathered data gathered in the short-term that is averaged to better determine the profile of the user. As described below, the short-term comparison and long-term comparison user profile can be compared to either help to aid in the short-term profile, e.g. if the user always shouts, shouting in the short-term should not indicate anger.

Figure 6:
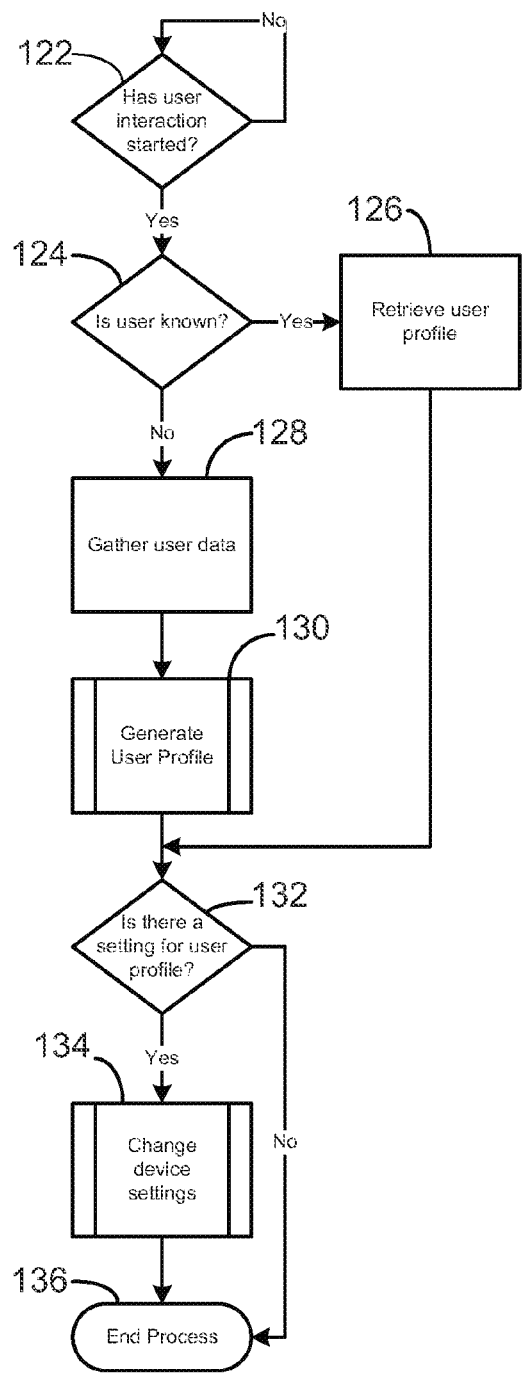
FIG. 6 is a flow chart illustrating one embodiment of the method to generate a user profile and change settings in accordance therewith at a wireless communication device.

In one embodiment shown in FIG. 6, the wireless communication device 12, 18, 20, 22 executes a method on the computer platform 62 thereof such that a user profile can be generated locally for a user. A determination is made, as shown at decision 122, as to whether the user interaction with the wireless communication device 12, 18, 20, 22 has started. If not, a wait state is entered until user interaction starts. Otherwise, if user interaction has started at decision 122, a determination is then made as to whether the user is known, as shown at decision 124. If the user is known at decision 124, the user profile is retrieved, as shown at step 126. Otherwise if the user is not known at decision 124, the user data is gathered, shown at step 128, and the user profile is generated, as shown at predefined process 130, which can be a personality profile, emotional state, medical profile, and the like. Then a determination is made as to whether there is a user profile setting for the wireless device based upon the user profile, as shown at decision 132. Decision 132 is also reached if a user profile was retrieved at step 126. If there is not a setting for the user at decision 132, then the process ends, as termination 136. Otherwise, if there is a setting for the user profile at decision 132, the wireless communication device 12, 18, 20, 22 settings are changed, as shown at predefined process 134, and then the process ends at termination 136.

FIGS. 7A and 7B is illustrate one embodiment of a method for sending user data from a wireless communication device 12, 18, 20, 22 to another computer device, such as user profile server 16, which is executing the process shown in FIG. 7B, to receive a user profile back from the other computer device. The wireless communication device 12, 18, 20, 22 determines an interaction with a user of that device has started, as shown at decision 150. This can be the user unlocking the phone with a pin, or starting to interact with the device functionality such as choosing a contact to dial or a PTT group to make a group call to. If no user interaction has started at decision 150, a wait state is entered until user interaction begins. If user interaction has started at decision 150, in step 152, the wireless communication device 12, 18, 20, 22 requests a user profile for the user from the user profile server 16, which will enter the process shown in FIG. 7B. The user is preferably determined with some specificity, such as being identified based upon pin entry, picture taken, voice capture, and the like, but the process could simply assume the identity of the user, such as assuming the user is the owner of the wireless communication device 12, 18, 20, 22, or the last user.

The process in FIG. 7A on the wireless communication device 12, 18, 20, 22 then makes a determination as to whether a user profile has been received for the user, as shown at decision 154. If a user profile has been received at decision 154, then the wireless device functionality settings are changed, as shown as predefined process 160, such as changing the UI, screen presentation, device volume, and the like, and the process then ends at termination 162, and the wireless communication device 162 will await another user interaction at decision 150. If a user profile has not been received at decision 154, then in step 156, the wireless communication device 12, 18, 20, 22 gathers the user data (as described in the various embodiments herein). The wireless communication device 12, 18, 20, 22 sends the gathered user data to the user profile server 16, as shown at step 158, and enters a loop at decision 154 to gather and send user data until ultimately receiving a user profile back from the user profile server 16.

In FIG. 7B, the process at the user profile server 16 in communication with the wireless communication device 12, 18, 20, 22 is shown. The user profile server 16 determines if the wireless communication device 12, 18, 20, 22 has requested a user profile, as shown at decision 170, and if no request has been made, the user profile server 16 will enter a wait state for the request at decision 170. Otherwise, once the user profile has been requested at decision 170, a determination is then made as to whether the user for which the user profile is requested is known, as shown at decision 172. If the user is known, the user profile is retrieved, as shown at step 174 and then sent back to the wireless communication device 12, 18, 20, 22. Otherwise, if the user is not known to the user profile server 16 at decision 172, the user profile server 16 will not send a user profile to the wireless communication device 12, 18, 20, 22 which will cause that device to start gathering and sending user data as shown in FIG. 7A, and the user profile server 16 will receive gathered user data, as shown at step 176, and then generate a user profile for the received user data, as shown as predefined process 178. The user profile server 16 then sends the generated user profile back to the wireless communication device 12, 18, 20, 22, and also stores the user profile, as shown at step 180, and the process then ends as shown at termination 182. The storage of the generated user profile, step 180, is preferable to create a database of user profiles, but is not required.

Figure 8:
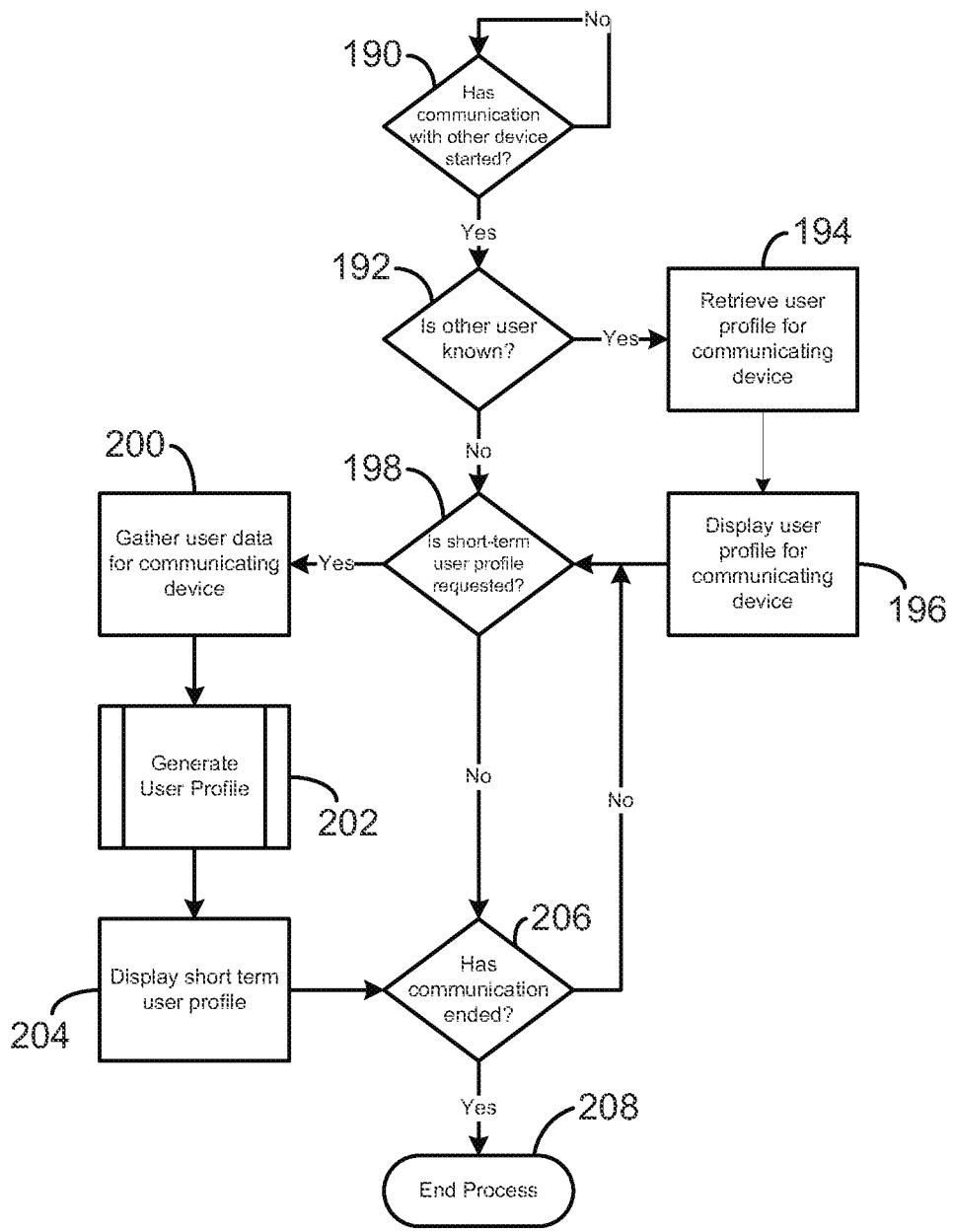
FIG. 8 is a flowchart for one embodiment of a method executing on a wireless communication device that allows either a stored user profile to be shown for the user of a communicating device, or a short-term profile can be alternately generated and displayed.

FIG. 8 is a flowchart for one embodiment of the method executing on a wireless communication device 12, 18, 20, 22 that allows either a stored user profile to be shown for the user of a device communicating with that wireless communication device 12, 18, 20, 22, or a short-term profile can be alternately generated and displayed, such as in the wireless communication devices 90 and 100 in FIG. 4, which are in engaged in a communication. The wireless communication device 12, 18, 20, 22 determines if a communication with another device has started, as shown at decision 190, and if no request has been made, the wireless communication device 12, 18, 20, 22 will enter a wait state for the communication to start at decision 190. Otherwise, once the communication has started at decision 190, a determination is then made as to whether the user for the other communication device is known, as shown at decision 192. If the user is known, the user profile for the other user is retrieved in step 194 and displayed, such as on display 92 of mobile phone 90, as shown at step 196. Otherwise, if the user is not known at decision 192, or after the user profile for the communicating user is displayed (step 196), a determination is then made as to whether a short-term profile of the other user is requested, as shown at decision 198.

If no short-term profile is requested at decision 198, a determination is then made as to whether the communication has ended, as shown at decision 206. Otherwise, if a short-term profile is requested by the user of the wireless communication device 12, 18, 20, 22 at decision 198, the user data is gathered for the communicating device, as shown at step 200, which can be data such as the caller's voice, a picture of the caller, and other medical data sent as described herein, or can alternately be the review of a specific user profile sent from the communicating device. Then a short-term user profile is generated, as shown at predefined process 202, and the short term profile is displayed, such as on display 92 on mobile phone 90, as shown as step 204. The short-term profile can be an emotional state, like that shown in FIG. 4, or personality profile (such as Myers-Briggs type), psychological profile, or medical information. The predetermined process 202 can also include the retrieval of a long-term profile for the user and comparison of the long-term profile data with the short-term data to note any anomalies, e.g. such as shouting when the user always shouts or grimacing when the user always grimaces. Such harmonization data from the comparison can also be stored to make a more accurate long-term user profile.

After the short-term profile has been displayed at step 204, the determination as to whether that communication has ended, decision 206, is made. If the communication has not ended at decision 206, the process returns to decision 198 to determine if the short-term user profile is still requested, and then will update the short-term profile accordingly. Otherwise, if the communication has ended as decision 206, the process ends as shown at termination 208.

Other changes in the system 10 and methods shown herein will be apparent to those of skill in the art. For example, the method shown on the wireless communication device 12,18, 20,22 in FIG. 8 could likewise be implemented with a user profile server 16, similarly to the method shown in FIGS. 7A and 7B, but with the user profile server 16 supplying short-term user profiles to the wireless communication device 12,18,20,22. Furthermore, more than two computer devices can be used in the present system and method, and accordingly, such implementation is readily scalable. And the wireless communication device 12,18,20,22 could likewise show many communicating devices and their user profiles at once, such as in a group communication (PTT call).

It can be seen that the wireless device 12,18,20,22 accordingly provides an inventive method of profiling a user of a wireless communication device 12,18,20,22 and potentially altering the wireless communication device functionality based upon the user profile, through, in one embodiment, the gathering of user data from physical user interaction with the wireless communication device 12,18,20,22, or alternately, the user data can come from another computer device in communication therewith, such as the user profile server 16. A user profile is then created as based upon the gathered user data, and the wireless communication device functionality altered based upon the gathered user data. Alternately, the user profile can be displayed to the user, such as shown in display 54 in FIG. 3.

The gathering of user data can based upon interpretation of short-term data input by the user into the wireless communication device 12,18,20,22, as shown in FIG. 8, or alternately, can be based upon interpretation of long-term data input by the user into the wireless communication device 12,18,20,22 over time, which can provide a more accurate user profile be eliminating anomalies in the data. The gathering of user data is based upon interpretation of user physical interaction with one or more data input mechanisms of the wireless communication device 12,18,20,22, such as through speaking in the microphone 98, taking a picture through a camera 94, or even from a medical device, such as remote earpiece 104.

In view of the methods being executable on a mobile device and other computer platforms, the method can accordingly be performed by a program resident in a non-transitory computer readable medium, where the program directs the mobile device or other computer device having a computer platform to perform the steps of the method. The non-transitory computer readable medium can be the memory of the server, or can be in a connective database. Further, the non-transitory computer readable medium can be in a secondary storage media that is loadable onto a wireless communications device computer platform, such as a magnetic disk or tape, optical disk, hard disk, flash memory, or other storage media as is known in the art.

In one or more exemplary embodiments, the functions described may be implemented in hardware, software, firmware, or any combination thereof. If implemented in software, the functions may be stored as one or more instructions or code on a non-transitory computer-readable medium. Non-transitory computer-readable media includes computer storage media, including any medium that facilitates transfer of a computer program from one place to another. A storage media may be any available media that can be accessed by a computer. By way of example, and not limitation, such non-transitory computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of non-transitory computer-readable media.

While the invention has been particularly shown and described with reference to a preferred embodiment thereof, it will be understood by those skilled in the art that various changes in form and detail may be made without departing from the scope of the present invention as set forth in the following claims. Furthermore, although elements of the invention may be described or claimed in the singular, the plural is contemplated unless limitation to the singular is explicitly stated.

What is claimed is:

1. A method of altering functionality of a wireless communication device, comprising:
    gathering user data from a physical user interaction with a first wireless communication device;
    transmitting the gathered user data to a second wireless communication device;
    creating a user profile in the second wireless communication device based upon the gathered user data; and
    altering a functionality of the second wireless communication device based upon the user profile.

2. The method of claim 1, wherein creating a user profile based upon the gathered user data comprises interpreting data received as a user input to the first wireless communication device.

3. The method of claim 1, wherein creating a user profile based upon the gathered user data comprises interpreting short-term data received as a user input to the first wireless communication device.

4. The method of claim 1, wherein creating a user profile based upon the gathered user data comprises interpreting long-term data received as a user input to the first wireless communication device.

5. The method of claim 1, wherein creating a user profile based upon the gathered user data comprises interpreting contact list information.

6. The method of claim 1, wherein creating a user profile based upon the gathered user data comprises interpreting a number of members of one or more communication groups with which the first wireless communication device is associated.

7. The method of claim 1, wherein creating a user profile based upon the gathered user data comprises interpreting a user physical interaction with one or more data input mechanisms of the first wireless communication device.

8. The method of claim 1, wherein creating a user profile based upon the gathered user data comprises interpreting physical information collected regarding a user of the first wireless communication device.

9. The method of claim 1, wherein:
    the first wireless communication device comprises a camera; and
    creating a user profile based upon the gathered user data comprises interpreting a picture taken of a user by the camera of the first wireless communication device.

10. The method of claim 1, wherein creating a user profile based upon the gathered user data comprises interpreting a volume of a user's speech.

11. The method of claim 1, wherein creating a user profile comprises performing a psychological evaluation based upon the gathered user data.

12. The method of claim 1, wherein altering the functionality of the second wireless communication device comprises altering a graphic user interface (GUI) of the second wireless communication device.

13. The method of claim 1, wherein creating a user profile based upon the gathered user data comprises interpreting medical data gathered regarding a user by a medical diagnostic tool.

14. The method of claim 13, wherein interpreting medical data comprises making a medical diagnosis based upon the gathered user data.

15. The method of claim 13, wherein:
    gathering user data from the physical user interaction with the first wireless communication device comprises gathering data from an external medical device coupled to the first wireless communication device via a wireless communication link; and
    interpreting medical data comprises interpreting medical data gathered from the external medical device.

16. A communication device, comprising:
    a transceiver;
    a memory; and
    a processor coupled to the memory and the transceiver, wherein the processor is configured with processor-executable instructions to perform operations comprising:
        receiving user data gathered from a physical user interaction between a user and a second wireless communication device;
        creating a user profile based upon the gathered user data; and
        altering a functionality of the communication device based upon the user profile.

17. The communication device of claim 16, wherein the processor is configured with processor-executable instructions such that creating a user profile based upon the gathered user data comprises interpreting data input by the user into the second wireless communication device.

18. The communication device of claim 16, wherein the processor is configured with processor-executable instructions such that creating a user profile based upon the gathered user data comprises interpreting short-term data input by the user into the second wireless communication device.

19. The communication device of claim 16, wherein the processor is configured with processor-executable instructions such that creating a user profile based upon the gathered user data comprises interpreting long-term data input by the user into the second wireless communication device.

20. The communication device of claim 16, wherein the processor is configured with processor-executable instructions such that creating a user profile based upon the gathered user data comprises interpreting contact list information received from the second wireless communication device.

21. The communication device of claim 16, wherein the processor is configured with processor-executable instructions such that creating a user profile based upon the gathered user data comprises interpreting a number of members of a plurality of communication groups with which the second wireless communication device is associated.

22. The communication device of claim 16, wherein the processor is configured with processor-executable instructions such that creating a user profile based upon the gathered user data comprises interpreting user physical interaction with a data input mechanism of the second wireless communication device.

23. The communication device of claim 16, wherein the processor is configured with processor-executable instructions such that creating a user profile based upon the gathered user data comprises interpreting physical information collected regarding the user of the second wireless communication device.

24. The communication device of claim 16, wherein the processor is configured with processor-executable instructions such that creating a user profile based upon the gathered user data comprises interpreting a picture taken of the user of the second wireless communication device.

25. The communication device of claim 16, wherein the processor is configured with processor-executable instructions such that creating a user profile based upon the gathered user data comprises interpreting a volume of the user's speech received by a microphone of the second wireless communication device.

26. The communication device of claim 16, wherein the processor is configured with processor-executable instructions such that creating a user profile comprises performing a psychological evaluation based upon the gathered user data.

27. The communication device of claim 16, further comprising a graphic user interface (GUI), wherein the processor is configured with processor-executable instructions such that altering the functionality of the communication device comprises altering the GUI of the communication device.

28. The communication device of claim 16, wherein the processor is configured with processor-executable instructions such that creating a user profile based upon the gathered user data comprises interpreting medical data gathered regarding the user of the second wireless communication device by a medical diagnostic tool.

29. The communication device of claim 28, wherein the processor is configured with processor-executable instructions such that interpreting medical data comprises making a medical diagnosis.

30. The communication device of claim 28, wherein:
the processor is configured with processor-executable instructions such that interpreting medical data comprises interpreting medical data gathered from an external medical device coupled to the second wireless communication device via a wireless communication link; and
interpreting medical data gathered from the external medical device comprises interpreting data received by the second wireless communication device over the wireless communication link.

31. A non-transitory computer readable storage medium having stored thereon processor-executable software instructions configured to cause a processor to perform operations comprising:

receiving user data gathered from a physical user interaction between a user and a first wireless communication device;
creating a user profile based upon the gathered user data; and
altering a functionality of a second wireless communication device based upon the user profile.

32. The non-transitory computer readable storage medium of claim 31, wherein the stored processor-executable software instructions are configured to cause a processor to perform operations such that creating a user profile comprises interpreting data input by the user into the first wireless communication device.

33. The non-transitory computer readable storage medium of claim 31, wherein the stored processor-executable software instructions are configured to cause a processor to perform operations such that creating a user profile comprises interpreting short-term data input by the user into the first wireless communication device.

34. The non-transitory computer readable storage medium of claim 31, wherein the stored processor-executable software instructions are configured to cause a processor to perform operations such that creating a user profile comprises interpreting long-term data input by the user into the first wireless communication device.

35. The non-transitory computer readable storage medium of claim 31, wherein the stored processor-executable software instructions are configured to cause a processor to perform operations such that creating a user profile comprises interpreting data obtained from a contact list stored in a memory of the first wireless communication device.

36. The non-transitory computer readable storage medium of claim 31, wherein the stored processor-executable software instructions are configured to cause a processor to perform operations such that creating a user profile comprises interpreting a number of members of a plurality of communication groups with which the first wireless communication device is associated.

37. The non-transitory computer readable storage medium of claim 31, wherein the stored processor-executable software instructions are configured to cause a processor to perform operations such that creating a user profile comprises interpreting physical user interactions with a data input mechanism of the first wireless communication device.

38. The non-transitory computer readable storage medium of claim 31, wherein the stored processor-executable software instructions are configured to cause a processor to perform operations such that creating a user profile comprises interpreting physical information gathered from the user of the first wireless communication device.

39. The non-transitory computer readable storage medium of claim 31, wherein the stored processor-executable software instructions are configured to cause a processor to perform operations such that creating a user profile comprises interpreting a picture taken of the user of the first wireless communication device.

40. The non-transitory computer readable storage medium of claim 31, wherein the stored processor-executable software instructions are configured to cause a processor to perform operations such that creating a user profile comprises interpreting speech volume of the user of the first wireless communication device.

41. The non-transitory computer readable storage medium of claim 31, wherein the stored processor-executable software instructions are configured to cause a processor to perform operations such that creating a user profile comprises performing a psychological evaluation based upon the gathered user data.

42. The non-transitory computer readable storage medium of claim 31, wherein the stored processor-executable software instructions are configured to cause a processor to perform operations such that altering the functionality of the second wireless communication device comprises altering a graphic user interface (GUI) of the second wireless communication device.

43. The non-transitory computer readable storage medium of claim 31, wherein the stored processor-executable software instructions are configured to cause a processor to perform operations such that creating a user profile comprises interpreting medical data gathered regarding the user of the first wireless communication device by a medical diagnostic tool.

44. The non-transitory computer readable storage medium of claim 43, wherein the stored processor-executable software instructions are configured to cause a processor to perform operations such that creating a user profile comprises making a medical diagnosis.

45. The non-transitory computer readable storage medium of claim 43, wherein the stored processor-executable software instructions are configured to cause a processor to perform operations such that interpreting medical data comprises interpreting medical data gathered from an external medical device coupled to the first wireless communication device over a wireless communication link.

46. A communication device configured for profiling a user to alter its functionality, comprising:
    means for receiving user data gathered from a physical user interaction with a second wireless communication device;
    means for creating a user profile based upon the gathered user data; and
    means for altering the functionality of the communication device based upon the user profile.

47. The communication device of claim 46, wherein means for creating a user profile based upon the gathered user data comprises means for interpreting data received as a user input on the second wireless communication device.

48. The communication device of claim 46, wherein means for creating a user profile based upon the gathered user data comprises means for interpreting short-term data received as user input on the second wireless communication device.

49. The communication device of claim 46, wherein means for creating a user profile based upon the gathered user data comprises means for interpreting long-term data received as user input on the second wireless communication device.

50. The communication device of claim 46, wherein means for creating a user profile based upon the gathered user data comprises means for interpreting information relating to a contact list stored in a memory of the second wireless communication device.

51. The communication device of claim 46, wherein means for creating a user profile based upon the gathered user data comprises means for interpreting a number of members of one or more communication groups with which the second wireless communication device is associated.

52. The communication device of claim 46, wherein means for creating a user profile based upon the gathered user data comprises means for interpreting user physical interaction with one or more data input mechanisms of the second wireless communication device.

53. The communication device of claim 46, wherein means for creating a user profile based upon the gathered user data comprises means for interpreting physical information collected regarding the user of the second wireless communication device.

54. The communication device of claim 46, wherein means for creating a user profile based upon the gathered user data comprises means for interpreting a picture of the user of the second wireless communication device.

55. The communication device of claim 46, wherein means for creating a user profile based upon the gathered user data comprises means for interpreting a volume of user's speech received by a microphone of the second wireless communication device.

56. The communication device of claim 46, wherein means for creating a user profile comprises means for performing a psychological evaluation based upon the gathered user data.

57. The communication device of claim 46, wherein means for creating a user profile based upon the gathered user data comprises means for interpreting medical data gathered regarding the user of the second wireless communication device by a medical diagnostic tool.

58. The communication device of claim 57, wherein means for interpreting medical data comprises means for making a medical diagnosis.

59. The communication device of claim 57, wherein means for interpreting medical data comprises means for interpreting medical data collected from an external medical device coupled to the second wireless communication device via a wireless communication link.

60. A communication system, comprising:
    a first wireless communication device comprising a transmitter for transmitting wireless signals, a memory, and a processor coupled to the transmitter and the memory of the first wireless communication device; and
    a second wireless communication device comprising a receiver configured to received signals transmitted by the transmitter, a memory, and a processor coupled to the receiver and memory of the second wireless communication device,
    wherein the first wireless communication device processor is configured with processor-executable instructions to perform operations comprising:
        gathering user data from a physical user interaction; and
        transmitting the gathered user data to the second wireless communication device, and
    wherein the second wireless communication device processor is configured with processor-executable instructions to perform operations comprising:
        receiving the gathered user data transmitted by the first wireless communication device;
        creating a user profile based upon the gathered user data; and
        altering a functionality of the second wireless communication device based upon the user profile.

61. The communication system of claim 60, wherein the second wireless communication device processor is configured with processor-executable instructions to perform operations such that creating a user profile based upon the gathered user data comprises interpreting data received as a user input to the first wireless communication device.

62. The communication system of claim 60, wherein the second wireless communication device processor is configured with processor-executable instructions to perform operations such that creating a user profile based upon the gathered user data comprises interpreting short-term data received as a user input to the first wireless communication device.

63. The communication system of claim 60, wherein the second wireless communication device processor is configured with processor-executable instructions to perform operations such that creating a user profile based upon the gathered user data comprises interpreting long-term data received as a user input to the first wireless communication device.

64. The communication system of claim 60, wherein the second wireless communication device processor is configured with processor-executable instructions to perform operations such that creating a user profile based upon the gathered user data comprises interpreting a contact list stored in the memory of the first wireless communication device.

65. The communication system of claim 60, wherein the second wireless communication device processor is configured with processor-executable instructions to perform operations such that creating a user profile based upon the gathered user data comprises interpreting a number of members of one or more communication groups with which the first wireless communication device is associated.

66. The communication system of claim 60, wherein the second wireless communication device processor is configured with processor-executable instructions to perform operations such that creating a user profile based upon the gathered user data comprises interpreting a user physical interaction with one or more data input mechanisms of the first wireless communication device.

67. The communication system of claim 60, wherein the second wireless communication device processor is configured with processor-executable instructions to perform operations such that creating a user profile based upon the gathered user data comprises interpreting physical information collected regarding a user of the first wireless communication device.

68. The communication system of claim 60, wherein the first wireless communication device further comprises a camera, and the second wireless communication device processor is configured with processor-executable instructions to perform operations such that creating a user profile based upon the gathered user data comprises interpreting a picture taken by the camera.

69. The communication system of claim 60, wherein the first wireless communication device further comprises a microphone, and the second wireless communication device processor is configured with processor-executable instructions to perform operations such that creating a user profile based upon the gathered user data comprises interpreting a volume of a user's speech received by the microphone.

70. The communication system of claim 60, wherein the second wireless communication device processor is configured with processor-executable instructions to perform operations such that creating a user profile comprises performing a psychological evaluation based upon the gathered user data.

71. The communication system of claim 60, wherein the second wireless communication device includes a graphic user interface (GUI) and the second wireless communication device processor is configured with processor-executable instructions to perform operations such that altering the functionality of the second wireless communication device comprises altering the GUI of the second wireless communication device.

72. The communication system of claim 60, wherein the second wireless communication device processor is configured with processor-executable instructions to perform operations such that creating a user profile based upon the gathered user data comprises interpreting medical data gathered regarding a user of the first wireless communication device by a medical diagnostic tool.

73. The communication system of claim 72, wherein the second wireless communication device processor is configured with processor-executable instructions to perform operations such that interpreting medical data comprises making a medical diagnosis based upon the gathered user data.

74. The communication system of claim 72, wherein:
the second wireless communication device processor is configured with processor-executable instructions to perform operations such that interpreting medical data comprises interpreting medical data gathered from an external medical device coupled to the first wireless communication device via a wireless communication link; and
the first wireless communication device processor is configured with processor-executable instructions to perform operations such that gathering user data from the physical user interaction with the first wireless communication device comprises gathering data from the external medical device over the wireless communication link.

* * * * *